United States Patent [19]
Houston et al.

[11] Patent Number: 4,931,657
[45] Date of Patent: Jun. 5, 1990

[54] ON-LINE TEXTURE SENSING

[75] Inventors: Kevin C. D. Houston, Burnaby; Roman E. Popil, White Rock, both of Canada

[73] Assignee: MacMillan Bloedel Limited, Canada

[21] Appl. No.: 337,659

[22] Filed: Apr. 13, 1989

[51] Int. Cl.⁵ .............................................. G01N 21/88
[52] U.S. Cl. .................................. 250/559; 250/571; 250/225; 356/369
[58] Field of Search ............... 250/571, 572, 559, 560, 250/225; 356/73, 430, 369; 162/198

[56] References Cited

U.S. PATENT DOCUMENTS

| 4,506,980 | 3/1985 | Pryor et al. | 250/572 |
| 4,644,174 | 2/1987 | Ouellette et al. | 250/559 |
| 4,648,712 | 3/1987 | Bernholt | 356/73 |
| 4,760,271 | 7/1988 | Bernholt | 250/571 |

OTHER PUBLICATIONS

A Formation Tester which Graphically Records Paper Structure, Burkhard et al., Pulp and Paper Magazine of Canada, 60, No. 6, T319-T334 Jun., 1960).
Development of an On-Line Formation Tester to Determine Optimal Use of Retention Aids, Landmark et al., Paper Trade Journal, Sep. 1984, pp. 80 to 86.
Optical Measurement Throws New Light on Paper Surface, Hansuebasi and Morantz, Paper Technology in Industry, Aug., 1987.
Solid State Surface Inspection Equipment, P. W. Loose, Jun., 1987 TAPPI Journal, pp. 69 to 74.
On-Line Automatic Pulp Dirt Count Measurement, Kemeny et al., Tappi Conference proceedings, 1987, pp. 21-24.

Primary Examiner—David C. Nelms

[57] ABSTRACT

The texture of a travelling web is determined by instantaneously illuminating an area of the web via a strobe light and phtographing the illuminated area by a video camera correlated to operate in conjunction with the strobe. The signal from the camera is digitized, histogrammed and analyzed to determine the characteristics of the web. The strobe light may direct the light through the web or at an angle to the web and the video camera depending on the characteristics to be determined may be positioned to receive specularly reflected light from the web or reflected light or positioned on the opposite side the web to receive light transmitted through the web. In one embodiment the light is polarized and directed at Brewster's angle onto the surface of the web and only similarly polarized specularly reflected light is received by the camera.

10 Claims, 3 Drawing Sheets

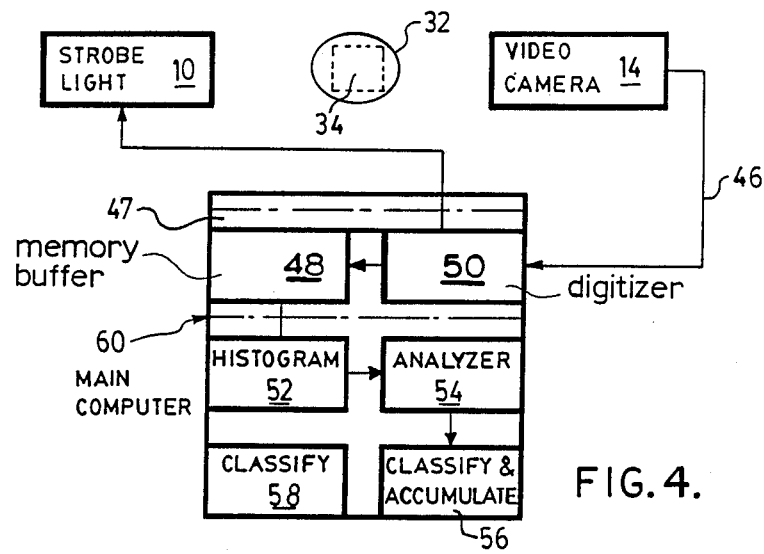
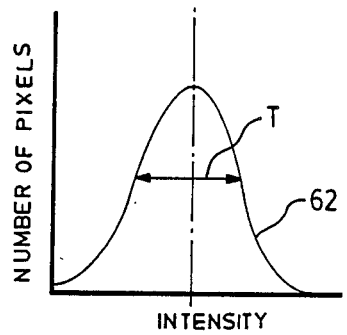
FIG. 5.
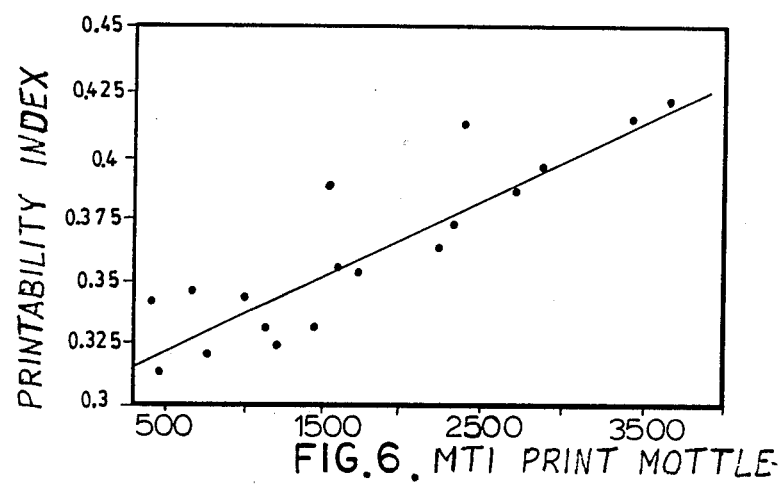
FIG. 6. MTI PRINT MOTTLE

ON-LINE TEXTURE SENSING

FIELD OF THE INVENTION

The present invention relates to web texture sensing. More particularly the present relates to texture sensors applying image analysis to instantaneous image signals generated by a video camera operated in synchronization with a strobe light.

BACKGROUND OF THE INVENTION

Many different instruments have been designed for on-line sensing of web characteristics. Such equipment particularly related to paper includes on-line sensors for paper formation, fibre orientation, wire mark, etc.

One of the earlier developments for detecting formation is described in a paper "A Formation Tester Which Graphically Records Paper Structure" by Burkhard et al published in the Pulp and Paper Magazine of Canada, 60, No. 6, T319-T334 (June 1960) wherein it was emphasized that direction was an important factor that had to be considered in an instrument for measuring paper structure. This device utilizes an illuminator and a photo electric cell to sense the amount of light transmitted through the web and generates a transmitted light signal which is analyzed in a frequency spectrum analyzer. The light source and photo electric cell move axially of a cylinder on which the paper sample is mounted.

A more recent system is described in an article entitled 'Development of an On-line Formation Tester to Determine Optimal Use of Retention Aids' by Landmark et al published in the Paper Trade Journal, Sept. 1984, pages 84 to 86. This system is based on the use of tester incorporating a laser and that was developed by the Norwegian Pulp and Paper Institute to measure the variations in basis weight. In particular for the instrument described by Landmark et al a specific laser was selected and illuminated a spot about one millimeter in diameter by directing light through the web, the light transmitted through the web was then projected onto a photo cell.

In U.S. Pat. No. 4,648,712 issued Mar. 10, 1987 to Bernholt a light source illuminates one side of the web and the radiation passing through the web is detected by a pair of detectors having fields of view along narrow strips which are perpendicular to each other. The detector outputs are processed to provide fibre orientation ratio, formation and basis weight measurements.

U.S. Pat. No. 4,760,271 issued July 26, 1988 to Bernholt describes a system, which like the above described Bernholt system, illuminates paper from one side and provides optical means on the opposite side for detecting the light transmitted through the paper. A second illuminator is provided on the same side of the paper as the detector and directs light onto the paper at an oblique angle to a line normal to the plane of the paper web and the reflected light emanating from the second source is also detected.

U.S. Pat. No. 4,644,174 issued Feb. 17, 1987 to Ouellette et al also describes directing a beam through the paper and utilizes a photo detector receiving the light transmitted through the paper in combination with a tuneable filter and a demodulator to produce a DC output reflecting size and distribution of fibers or flocs.

It is also known to measure the surface properties of paper by optical measurements. A recent technique for such optical measurement is described in a paper entitled 'Optical Measurement Throws New Light on Paper Surface' by Hansuebasi and Morantz published in Paper Technology in Industry, Aug. 1987. This technique employs a scanning goniometer which varies the angle of incidence of impingement of a polarized light and studies the angular reflectance and attempts to correlate printability with surface non-uniformity as determined by the equipment.

Equipment has also been proposed for surface inspection for defects wherein the entire surface web is scanned to detect defects or faults in the paper and enhanced graphics are used to visually display a defect such as a small tear or the like in the paper. Such a device described in a paper entitled 'Solid State Surface Inspection Equipment' by P. W. Loose published in June, 1987 Tappi Journal, pages 69 to 74. This system uses a line scan camera having a charged coupled device (CCD) and an electronic exposure control. The amount of light applied to the CCD of the camera is regulated and the basic scanning rate of the camera is synchronized with the web speed.

An on-line dirt counting systems is described in an article by Kemeny et al. entitled 'On-line Automatic Pulp Dirt Count Measurement' Tappi Conference proceedings, 1987, pages 2124 inclusive. The particular dirt counter described in this publication utilizes the CCD camera focused onto an illuminated surface of the pulp so that the light saturates the scanned segment of the pulp surface to eliminate any shadows which may tend to appear due to the roughness of the pulp surface. This device determines the dirt count by correlating the signal strength with a Base Line following threshold which was adjusted so that the system tracks around the normal product fluctuations and detects primarily sharp edge defects that generate a signal sufficiently high to trigger the system.

BRIEF DESCRIPTION OF THE PRESENT INVENTION

It is the main object of the present invention to provide a surface texture sensor to determine on-line the printability of a paper, for example as it is being produced.

It is a further object of the present invention to provide an optical system for on-line determination of formation of a paper web on-line.

Another object of the present invention is to provide an on-line monitor for the detection of the degree of calender blackening of a moving web. Calender blackening appears as translucent specks on the web caused by over densification of the paper structure in the calender nip.

It is a further object of the present invention to provide an optical on-line pulp sheet dirt monitor.

Broadly the present invention relates to an optical system for determining optical characteristics of a travelling web comprising strobe light means for instantaneously illuminating areas on an exposed surface of said web as said web traverses said strobe light means, video camera means focussed to view said areas when illuminated by said strobe light, means synchronizing the operation of said strobe with the operation of said camera to provide a video signal for each of said areas and means to analyze said signals to determine characteristics of said web.

Preferably said strobe light will direct a beam of light through said web from a second surface of said web said second surface being opposite said surface.

Most preferably said strobe light will project a beam of light onto said exposed surface of said web and will further include means for perpendicularly polarizing said light in a direction parallel to the plane of travel of said exposed surface thereby to illuminate each said area with light polarized parallel to the plain of said paper, said beam of light being directed to said paper at an angle within three (preferably less than one) degrees of the Brewster's angle for the material from which said web is made and said camera has its focal axis aligned to receive light reflected from said area at the specular angle of said polarized light and polarized in substantially the same plane as said polarized light projected onto said surface.

Preferably the longitudinal axis or direction of said beam of light and the focal axis of the camera will be in a plane perpendicular to the direction of travel of the web.

Preferably for determining printability the size of each said area will be coordinated with the size of the gloss mottle elements to be considered. For newsprint areas in the order of about 3 to 10 square centimeters are effective.

Said camera may be any suitable black and white or a color video camera preferably using a charge coupled device (CCD) as its pick-up.

To determine the printability of said web the signal from said video camera generated longitudinally specular polarized light will be digitized and a histogram formed of the degrees of brightness and the histogram analyzed to determine the distribution for degrees of brightness, a plurality of such distributions accumulated and a portion of the paper represented by said areas then classified as to surface texture.

To determine formation and blackening, the strobe light illuminates the web from one side of the web with the video camera directed at the opposite side of the web. Preferably the focal axis of the camera will be perpendicular to the surface of the web.

To determine the dirt count on a pulp sheet preferably the camera will be positioned with its focal axis perpendicular to the surface of the web and the web will be illuminated by a strobe light on the same side of the web as the camera so that the camera generates instantaneous signals of areas on the surface of said pulp sheet. The instantaneous signals are digitized and analyzed to determine number and preferably location of pixels in the camera illuminated below a certain threshold to provide a dirt count for the pulp sheet.

A BRIEF DESCRIPTION OF THE DRAWINGS

Further features, objects and advantages will be evident from the following detailed description of the preferred embodiments of the present invention taken in conjunction with the accompanying drawings in which FIG. 1 is a side elevation schematically illustrating a surface texture sensing device particularly useful in determining printability on-line.

FIG. 2 is a plan view illustrating the illuminated spot and the area viewed by the camera relative to the spot.

FIG. 3 schematically illustrates a system for traversing the sensor laterally of the direction of travel of paper web.

FIG. 4 is a schematic illustration of a suitable system for operating the present invention.

FIG. 5 illustrates a histogram of digitized light intensity data for signals of pixels in a single video frame developed by the camera.

FIG. 6 illustrates the correlation between detected gloss variation as determined by reflected light intensity distribution and a measure of conventional MTI print mottle of solid black prints.

Figure 8:
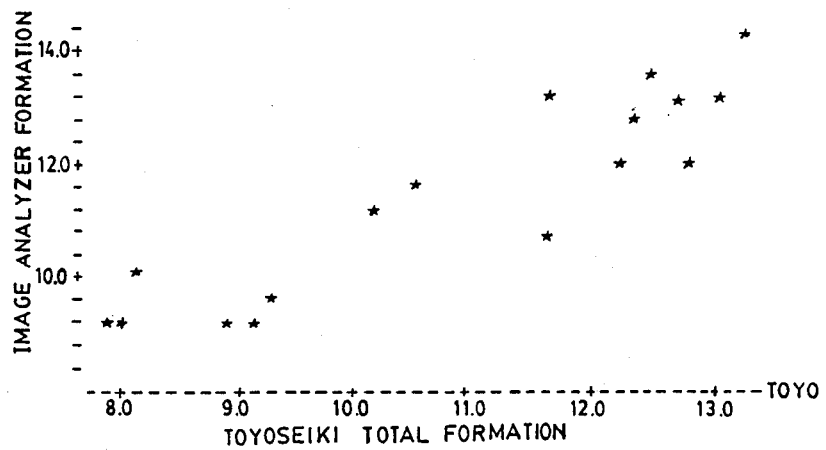

FIG. 8 in a plot of Formation as determined by the present invention against Toyoseiki total formation to illustrate the correlation.

PREFERRED EMBODIMENTS OF THE PRESENT INVENTION SURFACE TEXTURE OR PRINTABILITY SENSOR

One of the most important forms of the present invention is illustrated in FIGS. 1 to 6 inclusive and utilizes a system of sensing polarized light reflecting off the surface of the web to obtain a measure of large scale topography that effects print density uniformity. In particular the system schematically illustrated in FIG. 1 includes a strobe light 10 that directs a beam of light schematically indicated at 11 and is triggered via a strobe trigger system that synchronizes the operation of the light 10 and the video camera 14 as will be described in more detail herein below.

In the arrangement illustrated the beam of light 11 from strobe light 10 is polarized by a polarizing system 16 that polarizes the light perpendicular to the direction of the beam and in a direction parallel to the surface 18 of the paper web or the like 20 being scanned as indicated by the dots in the circle 22 indicating the light is polarized in the direction into the paper. This polarized light is directed to the surface 18 at an angle A which is substantially equal to Brewster's angle for the substrate 20 being examined.

The focal axis of the camera 14 as indicated by the line 24 is aligned with the specular angle for the light directed onto the surface 18 so that specular light reflected from the surface 18 is received by the camera. The reflected light transmitted to the camera is filtered by a polarizing system 26 which permits only light polarized in the same direction as the light issuing from the polarizer 16 to pass into the camera lens system as indicated by the dot in the circle 28.

The beam 11 and the focal axis 24 preferably will be in a plane substantially perpendicular to the direction of travel of the web 20.

Figure 1:
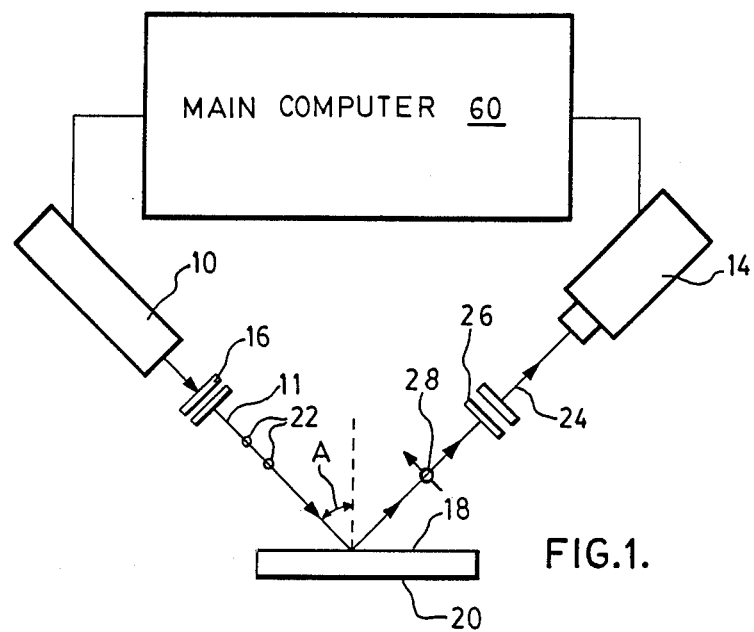
Figure 2:
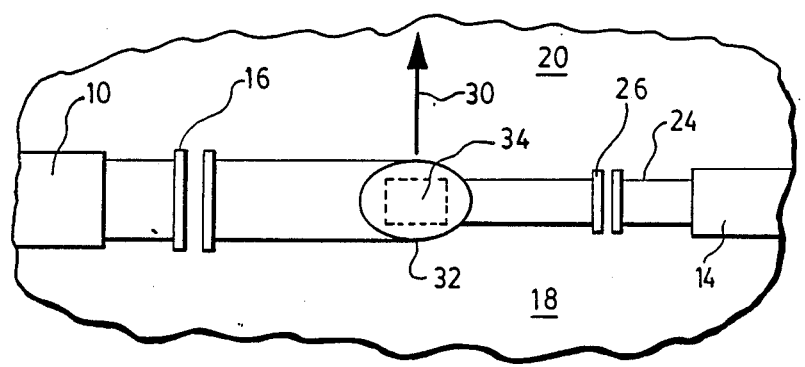
Figure 3:
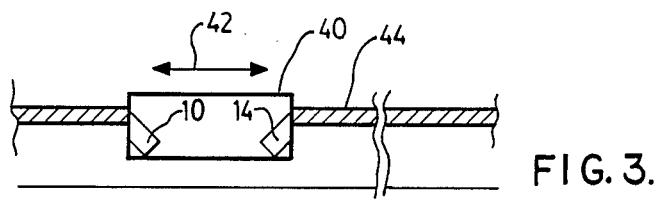

The web 20, as indicated in FIG. 2, is traveling in the direction of the arrow 30 and the strobe trigger activates the light 10 to instantaneously illuminate an area such as the area 32 in FIG. 2 with polarized light. The camera 14 is focussed upon and has a field of view equal to an area 34 indicated by the dash lines and contained within the illuminated area 32. The operation of the camera 14 and the strobe light 10 are coordinated so that the trigger triggers the strobe light 10 when the camera 14 is in condition to record a frame. The light 10 instantaneously illuminates the area 32 and the surface 18 of the web 20 is viewed by the camera 14 as a substantially stopped frame.

The size of the area 34 examined by the camera is determined by camera optics. Spatial resolution is determined by the area examined and the number of pixels in the camera pickup (e.g. charge coupled device (CCD)). The resolution selected will normally be in the range of about 0.1 to 0.5 millimeters on the surface of the web 18 and will depend on the characteristics being discriminated. It will be apparent that due to the angle of the focal axis of the camera to the surface of the sheet in FIG. 1 to 6 embodiment, the area 34 will be rectangular rather than square. When sensing printability or surface roughness this area 34 will normally be at least about 102 cm.

If the resolution is too small the variation in grey scale level which is formed into a histogram (to be described herein below) may be unnecessarily wide, in particular the individual pixels of the camera may register microscopic variations such as reflection from individual fibres, microscopic pin holes where there are no fibres, etc. It has been found that for all the instruments described herein, i.e. the surface sensor and the Formation, blackening and dirt counter to be described below, resolution generally should not be smaller than 0.1 mm, otherwise the microstructure Poisson distribution of individual fiber bundles is examined rather than the macroscale mass distribution that affects printability.

As above indicated the angle A is preferably substantially equal to Brewster's angle for the material being inspected. Although slight variations of up to about 3 degrees may be tolerated in the angle it is preferred to be within about 1° of Brewster's angle for the particular substrate being investigated. For paper Brewster's angle for cellulose has been found satisfactory.

If desired the instrument composed of the strobe light 10 and camera 14 may be mounted on a suitable carriage 40 which in turn is mounted on a suitable means 44 for moving the carriage 40 in the direction of the arrows 42 (generally substantially perpendicular to the direction of movement 30 of the web). Such a means 44 may take the form of a threaded rod or the like such as that illustrated at 44 in FIG. 3 which is threaded to the carriage so that rotation of the rod causes movement of the carriage axially of the rod 44.

Generally the area 32 is illuminated for a period of up to about 10 microseconds and preferably for about 3 microseconds with an intensity to significantly influence the pickup by the pixels in the camera sensor during the vertical blanking period, i.e. in the intervals when the pixels are not being read. The time period or duration of the illumination multiplied by the speed of the web being examined must be less than the image resolution if blurring is to be avoided. The CCD or camera pickup is not significantly influenced by the ambient light to which it is otherwise subjected. Not every frame needs to processed, and thus the strobe need not be triggered for each frame but for simplicity probably will. The more frequently data is collected the more information there is available, but also the more capacity required by the computer. In a conventional camera ½ of the pixels are read during one reading cycle and the remaining pixels on the next cycle so that any frame grab only obtains half the information. The output of ½ the pixels has been found to be satisfactory. It has been found that accumulating data and analyzing the data about every 1 to 2 seconds provides meaningful information upon which decisions may economically be based.

It is preferred to amplify the analog signal before it is converted to a digital signal as this improves the quality of the digitized signal under normal operating conditions. Furthermore the amplification maintains the analog signals within acceptable limits of the analog to digital (A/D) converter in the digitizer. A simple system for accomplishing this uses a commercial video digitizer board in conjunction with a personal computer for example, an AT type personal computer.

A histogram is used for determining printability, formation and blackening or dirt count as will be described herein below.

An electronic system suitable for carrying out the present invention is illustrated in FIG. 4. The strobe light 10 is triggered by a signal pulse taken from the video digitizer board 47 of the computer 60 and triggers the strobe light 10 in proper sequence with the video camera 14. The signal from the video camera 14 is carried via a line 46 to the main computer 60 incorporating the digitizer board 47 which may include a buffer 48. The signal is amplified in analog form and then digitized as indicated at 50. A histogram of the digitized signal is then produced as indicated at 52, the histogram is analyzed as indicated at 54, e.g. to determine the standard deviation. The analyzed frames of data from the camera 14 may then be accumulated in the accumulator 56 which classifies the data from each frame. Eventually, based on an accumulation of a suitable number of frames, (which number may be independently set) the area of the surface scanned is classified as will be discussed hereinbelow.

When measuring printability the histogram of each frame of data as indicated by the curve 62 in FIG. 5 is a plot of intensity versus frequency (number of pixels) and generally has a substantially Gaussian distribution for each image area 32. The standard deviation as indicated by the dimension T in FIG. 5 is determined and used to classify the particular frame as to its degree of printability. The larger the standard deviation T the poorer the printability of the sheet. Coefficient of Printability of the present invention is determined by the formula:

$$\text{Coefficient of Printability} = \frac{\text{Standard Deviation}}{\text{Mean}} \quad (1)$$

FIG. 6 shows a plot of MTI print mottle index versus relative gloss variation as designated by standard deviation (T) described above. Clearly there is a good correlation between the data generated using the on-line printability system described above and the conventional MTI print mottle index.

FORMATION TESTER

A different arrangement of similar equipment is required to measure Formation. In the arrangement as shown in the solid lines in FIG. 7, the strobe light 100 is positioned on one side of the paper web 102 and the camera 104 on the opposite side thereof. As with the previous discussed embodiment the operation of the strobe light 100 is correlated with that of the camera 104 and is triggered by a signal from the digitizer board 106 of the computer 110 so that the camera takes instantaneous video images of the instantaneously illuminated areas on the surface of the web 102 in the same manner as described above for the printability or surface texture sensor.

The frame data from the camera 104 which will examine an area 34 on the surface of the paper of at least about $10^2$ cm is amplified, as above described, in analog form and transmitted to a suitable computer 110 having a digitizer board 106 that may include a buffer 108, and is digitized by the digitizer 112 to provide a digitized signal for each frame. Histograms are developed in analyzer 114.

It is preferred to normalize the histogram and apply a gain adjustment factor "F" when it is desired to obtain the standard deviation as used for determining formation. The gain adjustment factor F is preferably determined by obtaining the mean intensity value (M) for each frame of data and then normalizing the data to a selected mean $M_s$. Generally the selected mean $M_s$ will be constant for all frames and will be selected based on the equipment and the expected intensity variations. The Factor F is determined by the formula:

$$F = M_s / M \qquad (2)$$

In a particular example given below the value selected as the normalized mean was $M_s = 100$ units when operating a video camera digitizer having a range of zero to 255 in intensity.

The standard deviation of the histogram preferably is then calculated incorporating the factor F and adjusted according to the following formula:

$$\text{Std. Dev.} = \left[ \frac{1}{\text{Total \# of Pixels}} \left[ \sum_{i=0}^{i=255} (i \times F - 100)^2 \times f_i \right] \right]^{\frac{1}{2}} \qquad (3)$$

where
i = grey level intensity varying from 0–255
$f_i$ = # of pixels with intensity i The use of the gain adjustment factor F in determining the standard deviation further compensates for changes in light fluctuations in color and/or intensity and further compensates for basis weight changes.

Figure 7:
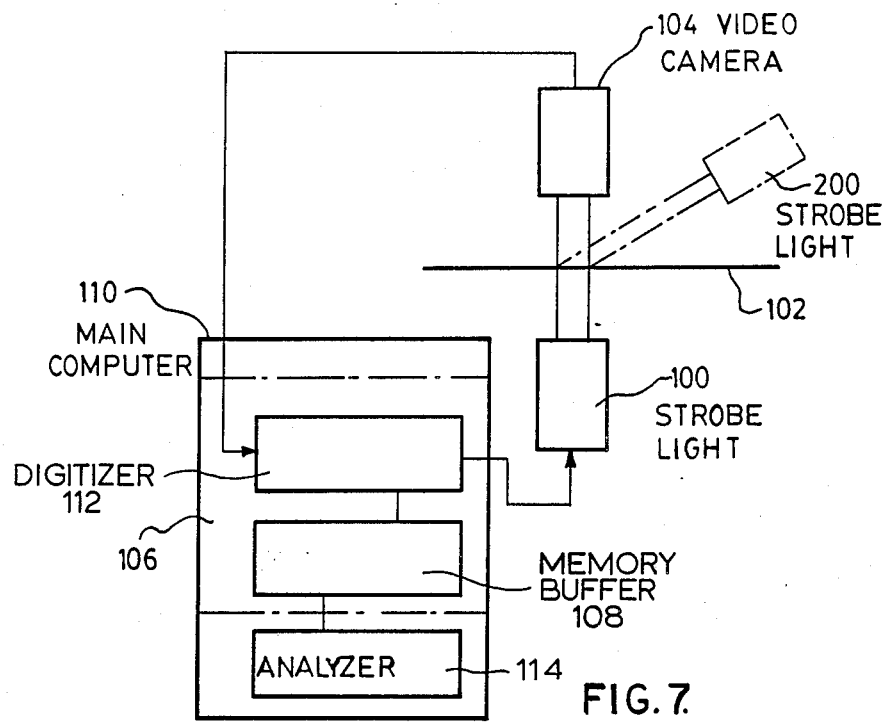
FIG. 7 illustrates a device for measuring formation and/or blackening and in dot/dash lines a device for detecting dirt.

In determining formation it has been found that the standard deviation T corresponded well with the Toyoseiki formation tester total variation value as illustrated in FIG. 7 or with the QNSM 'Lin C' value or the inverse of the M/K formation number. Generally the more concentrated the distribution, i.e. the smaller the Standard Deviation T, the better the Formation.

DIRT COUNTER

The dirt counter is very similar to the formation tester however the strobe light 100 is replaced by a strobe light 200 positioned above the web 102, i.e. on the same side of the web 102 as camera 104 so that light from the strobe directly illuminates the surface of the web 102 onto which the camera 104 is focussed (dash lines in FIG. 7). The operation of the strobe light 200 and of the camera 104 are synchronized so that the camera 104 generates frames of data when the surface is instantaneously illuminated by the strobe 200 in the same manner as described above with respect to the surface texture sensor or formation sensor. The data for these images is as above described amplified and transmitted to the main computer 110 into the buffer 108 and is then digitized to provide a digitized signal as indicated at 112 and the digitized signal preferably histogrammed as above described is analyzed in the analyzer 114 particularly to determine the number of areas or pixels of low reflectance below a certain selected threshold intensity level as defined by equation 4.

$$\% \text{ dirt} = \sum_{i=0}^{i=\text{threshold}} (f_i) \times \left( \frac{100}{\text{Total \# of pixels}} \right) \qquad (4)$$

where
i = intensity
$f_i$ = no. of pixels with intensity i

In this manner all of the pixels having an intensity below a preselected threshold level are counted as dirt particles based on the following:

The threshold for counting dirt is set at any preselected level but preferably will be a fixed fraction of the mean intensity level, for example threshold may be equal to the mean value of the histogram multiplied by a very small number that may be set by inspection of the segmented binary image to correspond with dirt specks on a pulp sheet.

The system may then be used to accept or reject depending on (a) the total area occupied by dirt particles or (b) the inclusion of significant large areas of a single dirt spot or any other suitable criteria that can be distinguished.

This technique may also be used with the strobe on the opposite side of the paper to the camera, i.e. strobe 100, only if the web transmits sufficient light.

It is also possible to detect plastic speck contaminants by substituting a source of infra red light for the strobe light and using the same analysis technique to determine the degree and location of plastic elements.

BLACKENING SENSOR

The blackening sensor uses essentially the same configuration and hardware as the formation sensor. To simplify the operation and accommodate differences in color light intensity and basis weight, the gain factor F as determined by formula (2) is employed in this case to modify the selected blackening threshold ($B_s$) to correspond with an operating blackening threshold (B)

$$B \text{ (operating threshold)} = \frac{B_s \text{ (selected blackening threshold)}}{F \text{ (factor)}} \qquad (5)$$

and percent blackening is given by the formula $$\% \text{ blackening} = \sum_{i=B}^{i=255} (f_i) \times \frac{100}{\text{Total \# of pixels}} \qquad (6)$$

where
$f_i$ is the number of pixels having an intensity of i
and
i = intensity.

Obviously the higher the % blackening, the poorer the paper quality.

All of the described embodiments are suitable for on-line sensing of selected parameters and may be coupled with other equipment for example on a paper machine to aid in control.

The preferred embodiments of the invention are illustrated by way of examples given herein above and it is to be understood that the descriptions and drawings are for the purposes of illustration and as an aid to understanding and not intended as a definition of the limits of the invention.

Modifications will be evident to those skilled in the art without department from the spirit of the invention as defined in the appended claims.

We claim:

1. An optical system for determining the texture of a travelling paper web comprising a strobe light means for instantaneously illuminating areas on a first surface of said web as said web traverses said strobe light means, means to polarize said light from said strobe means in a direction substantially parallel to the plane of travel of said web thereby to illuminate each said area with light polarized parallel to the plane of said web, said beam of light being, directed to said paper at an angle within 3 degrees of Brewster's angle for the paper, video camera means focused to view at least a portion of said areas when illuminated by said strobe light means, said camera means having its focal axis aligned to receive a specular light from said illuminated areas, polarized filter means to transmit to said camera only light polarized substantially parallel to the light polarized by said means to polarized said light thereby to provide video image signals representing said portions of said areas in substantially stop motion and means to analyze said video signals to determine texture characteristics of said web.

2. An optical system as defined in claim 1 wherein said strobe light means directs a beam of light through said web from a second surface of said web said second surface being opposite said first surface.

3. An optical system as defined in claim 1 wherein the longitudinal axis of said beam of light and said focal axis direct and receive light applied or reflected perpendicular to the direction of travel of said web.

4. An optical system as defined in claim 3 further comprising means to digitize each of said video image signals, means to form a histogram of such digitized video signals indicating degrees of brightness versus frequency, and means to analyze said histograms to determine the standard deviation of distribution of different brightness thereby to obtain a measure of printability of said paper web.

5. An optical system as defined in claim 4 further comprising means to accumulate a plurality of such distributions and to classify said areas of the web illuminated by said strobe as to its printability.

6. An optical system as defined in claim 1 further comprising means to digitize each of said video image signals, means to form a histogram of such digitized video signals indicating degrees of brightness versus frequency, and wherein said means to analyze analyses said histograms to determine the standard deviation of distribution of different brightness thereby to obtain a measure of printability of said paper web.

7. An optical system for determining the texture of a travelling paper web comprising a strobe light means for instantaneously illuminating areas on a first surface of said web as said web traverses said strobe light means, video camera means focused to view at least a portion of said areas when illuminated by said light means thereby to provide a video image signals representing said portions of said areas in substantially stop motion, means to digitize of said video image signals, means to form a histogram of such digitized video signals indicating degrees of brightness versus frequency, and means to analyze said histograms to determine the standard deviation of distribution of different brightness.

8. An optical system for determining the amount of dirt on a travelling cellulosic fibre web comprising a strobe light means for instantaneously illuminating areas on a first surface of said web as said web traverses said strobe light means, video camera means focused to view at least a portion of said areas when illuminated by said strobe light means thereby to provide a video image signals representing said portions of said areas in substantially stop motion, means to digitize said video image signals to provide a video signal and analysis means to analyze said video signals to determine the locations and sizes of areas on said web reflecting light of selected intensities relative to selected threshold intensity to obtain a measure of colour areas of the selected intensities in said web.

9. A system as defined in claim 8 wherein said web is a web of cellulosic pulp and wherein said strobe light means and said camera means are on the same side of said web.

10. An optical system for detecting plastic pieces in a travelling cellulosic fibre web comprising an infra red strobe light means for instantaneously illuminating areas on a first surface of said web with infra red light as said web traverses said strobe light means, video camera means focused to view at least a portion of said areas when illuminated by said strobe light means thereby to provide a video image signals representing said portions of said areas in substantially stop motion, means to digitize said video image signals to provide video signals and analysis means to analyze said video signals to determine the locations and size of areas on said web reflecting infra red light having an intensity below a selected threshold thereby to detect plastic in said pulp.

* * * * *